US008824633B2

(12) United States Patent
Ohishi

(10) Patent No.: US 8,824,633 B2
(45) Date of Patent: Sep. 2, 2014

(54) MEDICAL IMAGE PROCESSING APPARATUS AND CONTROL METHOD THEREOF

(75) Inventor: Satoru Ohishi, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 644 days.

(21) Appl. No.: 12/858,719

(22) Filed: Aug. 18, 2010

(65) Prior Publication Data

US 2011/0044525 A1 Feb. 24, 2011

(30) Foreign Application Priority Data

Aug. 19, 2009 (JP) .................................. 2009-190199

(51) Int. Cl.
*G06K 9/00* (2006.01)
*A61B 6/00* (2006.01)

(52) U.S. Cl.
CPC .............. *A61B 6/4014* (2013.01); *A61B 6/504* (2013.01); *A61B 6/4441* (2013.01); *A61B 6/547* (2013.01); *A61B 6/5235* (2013.01); *A61B 6/4225* (2013.01); *A61B 6/463* (2013.01); *A61B 6/466* (2013.01)
USPC ........................................... 378/92; 382/132

(58) Field of Classification Search
CPC .... A61B 6/4014; A61B 6/5235; A61B 6/463; A61B 6/524; A61B 6/547; G06K 9/00
USPC .................. 378/92–98.12; 382/128, 130–132
See application file for complete search history.

(56) References Cited

U.S. PATENT DOCUMENTS

| 7,130,378 B2 * | 10/2006 | Akutsu et al. ................. 378/117 |
| 2004/0079232 A1 * | 4/2004 | Groh et al. ........................... 96/1 |
| 2005/0008219 A1 * | 1/2005 | Pomero et al. ................ 382/154 |

FOREIGN PATENT DOCUMENTS

| JP | 01-185246 A | 7/1989 |
| JP | 9-187448 | 7/1997 |
| JP | 2001-137222 A | 5/2001 |
| JP | 2007-268060 | 10/2007 |
| JP | 2009-60953 | 3/2009 |

OTHER PUBLICATIONS

Office Action issued Mar. 11, 2014 in Japanese Patent Application No. 2010-183036.

* cited by examiner

*Primary Examiner* — Allen C. Ho
*Assistant Examiner* — Danielle Fox
(74) *Attorney, Agent, or Firm* — Oblon, Spivak, McClelland, Maier & Neustadt, L.L.P.

(57) ABSTRACT

An embodiment of the present invention provides a medical apparatus which displays an image of an object collected by using a first radiography system and a second radiography system, including: an image processing unit adapted to acquire a three-dimensional image; a projection direction input unit used to input a projection direction for at least one of the first radiography system and the second radiography system using the three-dimensional image; an imaging direction setting unit adapted to set an imaging direction for at least one of the first radiography system and the second radiography system based on the projection direction; and an interference checking unit adapted to determine whether interference between the first radiography system and the second radiography system will occur if one of the first radiography system and the second radiography system corresponding to the set imaging direction is moved.

20 Claims, 7 Drawing Sheets

MEDICAL IMAGE PROCESSING APPARATUS AND CONTROL METHOD THEREOF

CROSS-REFERENCE TO RELATED APPLICATIONS

This application is based upon and claims the benefit of priority from Japanese Patent Application No. 2009-190199 filed on Aug. 19, 2009, the entire contents of which are incorporated herein by reference.

FIELD

Embodiments described herein relate generally to a medical image processing apparatus and a control method thereof.

BACKGROUND

In the treatment of a cerebral aneurysm, since the blood vessel system in the brain is structurally complicated, it is difficult to accurately assess the structure and nature of the lesion using typical angiography. Thus, it is desired to represent the blood vessels three-dimensionally. X-ray angiography apparatus check condition of a blood vessel in the body of a patient by inserting a catheter into the blood vessel, injecting a contrast medium, and taking X-ray radiographs using angiography. With the X-ray angiography apparatus, blood vessel images shot by an X-ray radiography apparatus are transmitted to a medical image processing apparatus, reconstructed into three-dimensional image data by the medical image processing apparatus, and displayed on a monitor as 3D-DSA (Digital Subtraction Angiography) images. An observation angle of the blood vessel can be changed by rotating the 3D-DSA image on the monitor of the medical image processing apparatus using a mouse or the like.

Once the observation angle of the blood vessel is determined on the 3D-DSA image displayed on the monitor of the medical image processing apparatus, the observation angle is transmitted to the X-ray radiography apparatus. A radiography unit of the X-ray radiography apparatus moves to a position corresponding to the received observation angle. This function is called "angle feedback."

Generally, X-ray angiography apparatus for cerebral blood vessels are often a biplane type capable of taking angiograms simultaneously from two directions using two radiography systems. A radiography system set up in a front direction of an object laid face-up on a patient table is referred to as a frontal radiography system and a radiography system set up in a lateral direction of the object is referred to as a lateral radiography system.

The frontal radiography system includes a C-arm supported by a floor-mounted stand as well as an X-ray tube and X-ray detector mounted at opposite ends of the C-arm. The lateral radiography system includes a Ω-arm suspended from a ceiling as well as an X-ray tube and X-ray detector mounted at opposite ends of the Ω-arm.

Japanese Patent Laid-Open No. 9-187448 discloses a technique for performing quantitative analysis of an object's area to be diagnosed based on an image shot by biplane angiography and correcting results of the quantitative analysis using geometric magnification.

In the case of biplane angiography, to set both frontal and lateral radiography systems to appropriate observation angles, it is necessary to set the angles from an external apparatus. However, conventionally the "angle feedback" function works only in a single direction. Consequently, for example, if the observation angle of only the frontal radiography system is set using the "angle feedback" function, the observation angle of the lateral radiography system to be set is found using a 3D-DSA image and then the arm is set manually. This is very troublesome. Also, since both the frontal radiography system and lateral radiography system are moved, there is a problem of interference depending on positions of the two systems. In particular, when the angle of the lateral radiography system is set manually, it is difficult to find angles at which interference occurs. This makes it necessary to change the angle each time interference occurs.

DETAILED DESCRIPTION

According to an embodiment of the present invention, there is provided a medical apparatus which displays an image of an object collected by using a first radiography system and a second radiography system, including: an image processing unit adapted to acquire a three-dimensional image; a projection direction input unit used to input a projection direction for at least one of the first radiography system and the second radiography system using the three-dimensional image; an imaging direction setting unit adapted to set an imaging direction for at least one of the first radiography system and the second radiography system based on the projection direction; and an interference checking unit adapted to determine whether interference between the first radiography system and the second radiography system will occur if one of the first radiography system and the second radiography system corresponding to the set imaging direction is moved. Now, the embodiment of the present invention will be described below with reference to the accompanying drawings.

Figure 1:
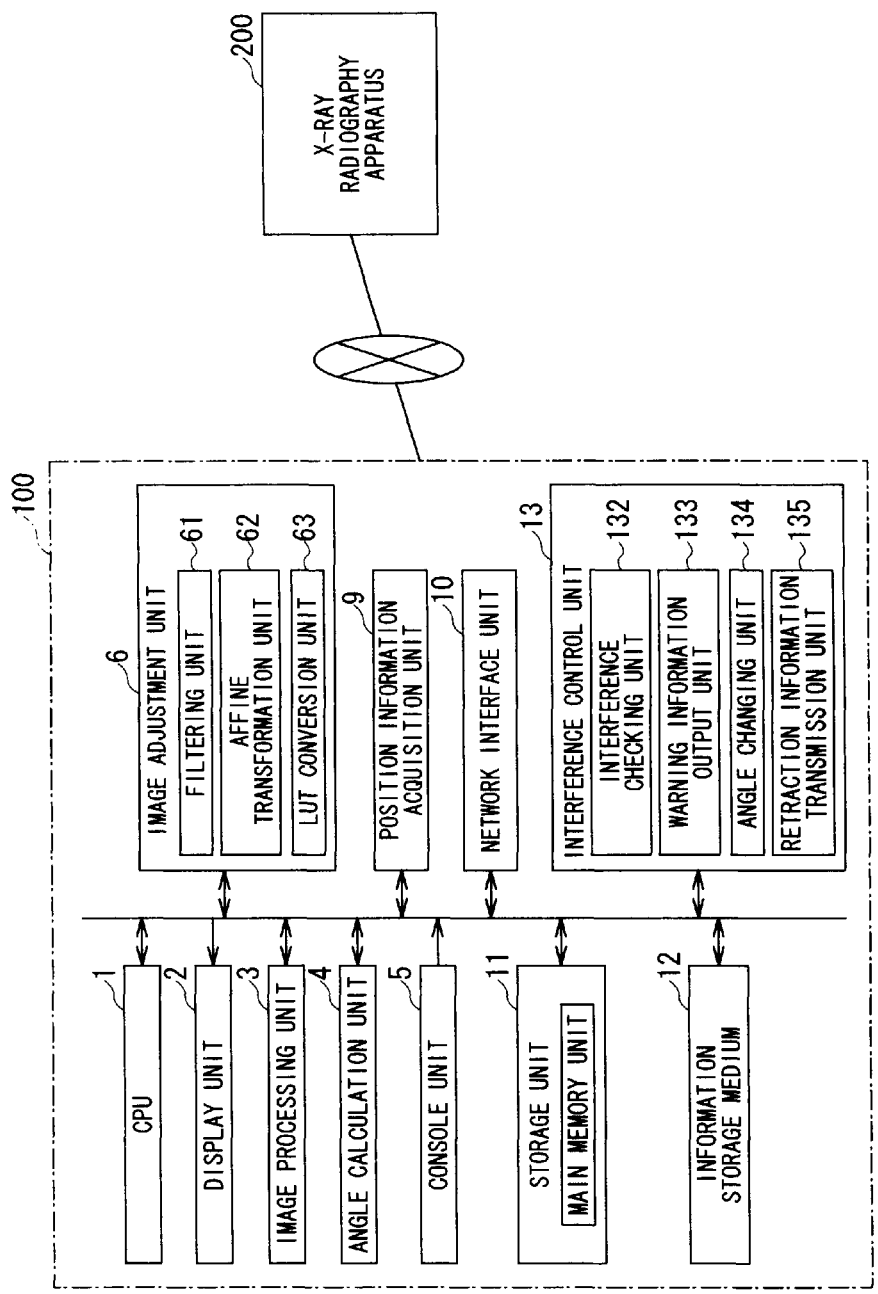
FIG. 1 is a block diagram showing a simplified configuration of a medical image processing apparatus according to an embodiment of the present invention.

FIG. 1 is a block diagram showing a simplified configuration of a medical image processing apparatus 100 according to the embodiment of the present invention. The medical image processing apparatus 100 is connected with an X-ray radiography apparatus 200 via an intranet.

The X-ray radiography apparatus 200, which supports biplane, includes a frontal X-ray radiography system (hereinafter referred to as a frontal radiography system 230 or simply as an F-side system) and lateral X-ray radiography system (hereinafter referred to as a lateral radiography system 210 or simply as an L-side system). The medical image processing apparatus 100 includes a CPU (Central Processing Unit) 1, display unit 2, image processing unit 3, angle calculation unit 4, console unit 5, image adjustment unit 6, position information acquisition unit 9, network interface unit 10, storage unit 11, information storage medium 12, and interference control unit 13, all of which are communicably interconnected via a bus.

Figure 2:
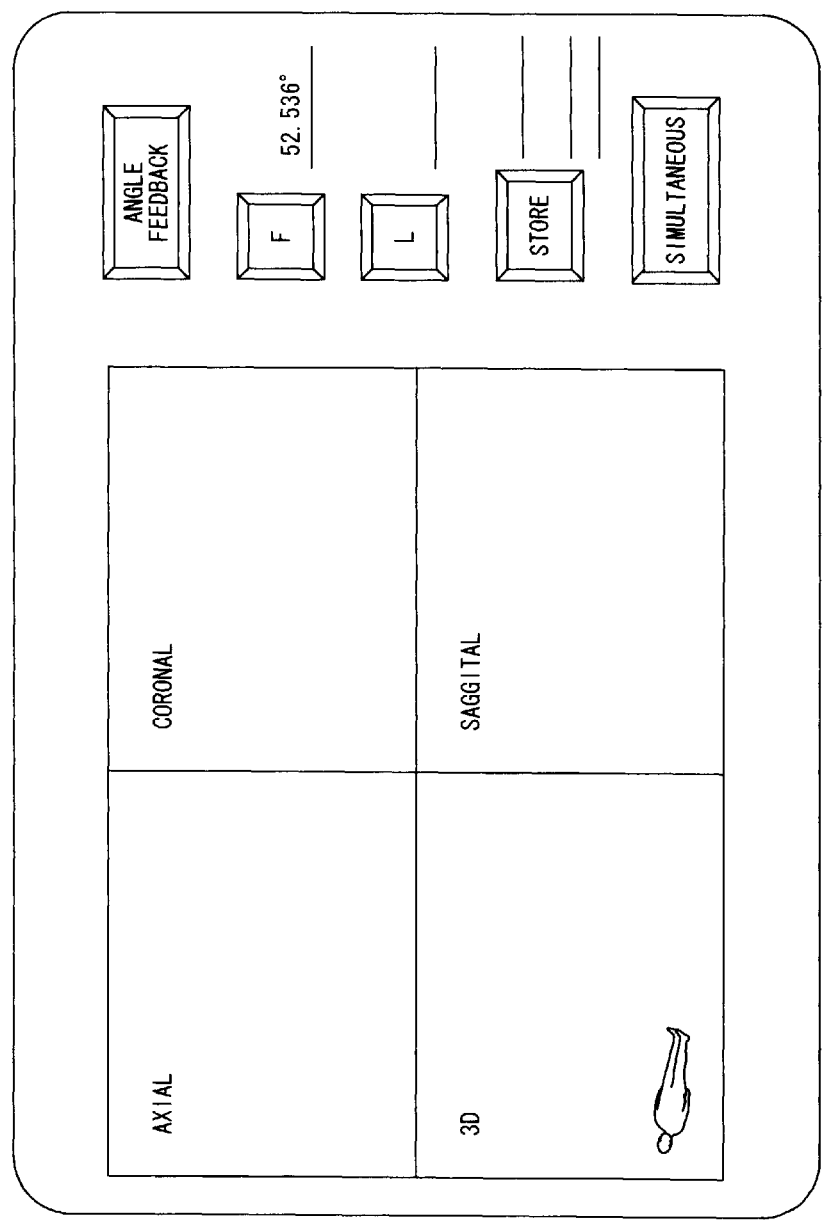
FIG. 2 is a diagram showing a display example of a display unit according to the embodiment of the present invention.

FIG. 2 shows a display example of the display unit 2. The display unit 2 displays various images and operation keys on a screen. On the right side of the screen, the display unit 2 displays "ANGLE FEEDBACK," "F," "L," and "STORE" keys in order from the top. On the left side of the screen, the display unit 2 displays a four-part split screen. Among the keys on the right side of the screen, the "F" and "L" keys are pressed to enter angles for the frontal radiography system 230 and lateral radiography system 210, respectively, based on an image displayed on the screen, the "STORE" key is used to store an inputted angle in the storage unit 11, and the "ANGLE FEEDBACK" key is used to transmit the angle stored using "STORE" to the X-ray radiography apparatus 200. F-side and L-side angles are displayed to the right of the "F" and "L" keys, respectively. Also, the angles at which the frontal radiography system 230 and lateral radiography system 210 are set when the "STORE" key is pressed are displayed to the right of the "STORE" key.

The four-part split screen displays "AXIAL," "CORONAL," "SAGGITAL," AND "3D" images (e.g., perspective views or volume-rendered images) clockwise from top left. In lower part of the "3D" section, a three-dimensional image which approximately represents the whole body of an object is displayed in a reduced size as an icon. The icon is linked to the image displayed in the "3D" section and indicates in what orientation the whole body of the object is shown by the image. The four sections display images outputted from the image processing unit 3. Incidentally, the display unit 2 may be a touch panel.

The image processing unit 3 performs three-dimensional image processing and the like on a 3D-DSA image received from the X-ray radiography apparatus 200 via the network interface unit 10 and displays the 3D-DSA image in a predetermined location of the display unit 2.

The console unit 5 is an interface which includes, for example, a keyboard and mouse, and is used by a user to enter various commands. Also, the console unit 5 allows the three-dimensional image displayed in the "3D" section of the display unit 2 to be rotated or moved from side to side and up and down by dragging or scrolling the mouse.

The angle calculation unit 4 calculates the F-side angle and L-side angle of the image displayed in the "3D" section of the display unit 2.

The image adjustment unit 6 includes a filtering unit 61, affine transformation unit 62, LUT (Look Up Table) conversion unit 63. The filtering unit 61 performs a filtering process such as high-frequency component enhancement filtering on 3D-DSA image data. The affine transformation unit 62 performs enlargement, expansion and contraction, and movement processes on the 3D-DSA image data. The LUT conversion unit 63 performs a tone conversion process on the 3D-DSA image data.

The position information acquisition unit 9 acquires position information (angles and positions) about the frontal radiography system 230 and lateral radiography system 210 of the X-ray radiography apparatus 200 (described later).

The network interface unit 10 communicates with the X-ray radiography apparatus 200 via a network such as a hospital intranet.

The interference control unit 13 includes an interference checking unit 132, warning information output unit 133, angle changing unit 134, and retraction information transmission unit 135 and controls interference between the radiography systems.

The interference checking unit 132 determines whether a first of the radiography systems will encounter interference from the second of the radiography systems if the angle of the first radiography system is changed. The warning information output unit 133 outputs warning information to the second radiography system or display unit 2 if the interference checking unit 132 determines that interference will occur. The angle changing unit 134 changes the angle of the first radiography system when the interference checking unit 132 determines that interference will occur. The retraction information transmission unit 135 transmits retraction information to the X-ray radiography apparatus 200 when the interference checking unit 132 determines that interference will occur, where the retraction information concerns, for example, a change in the angle of the second radiography system.

The storage unit 11 provides a work area for the CPU 1, network interface unit 10, and the like. Functions of the storage unit 11 can be implemented by a RAM (Random Access Memory). Also, the storage unit 11 stores the angles calculated by the angle calculation unit 4.

The information storage medium 12 (computer-readable medium) stores programs, data, and the like. Functions of the information storage medium 12 can be implemented by an optical disk (CD (Compact Disk)) or DVD (Digital Versatile Disk)), magneto-optical disk (MO), magnetic disk, hard disk, magnetic tape, memory (ROM: Read Only Memory), or the like. The CPU 1 performs various processes of the present embodiment based on the programs (data) stored in the information storage medium 12. That is, the information storage medium 12 stores the programs used to cause a computer to function as various units of the present embodiment (i.e., the programs which cause the computer to execute processes of the various units).

The CPU 1 comprehensively controls the medical image processing apparatus 100 and performs various other computational processes, control processes, and the like. Also, the CPU 1 performs necessary processes based on the programs and the like stored in the information storage medium 12. The CPU 1 performs various processes using a main memory unit in the storage unit 11 as a work area. Functions of the CPU 1 can be implemented by hardware or a program, where examples of the hardware include various processors (CPU, DSP (Digital Signal Processor), or the like), an ASIC (Application Specific Integrated Circuit) such as a gate array, an image processing board such as a GPU (Graphical Processing Unit).

Figure 3:
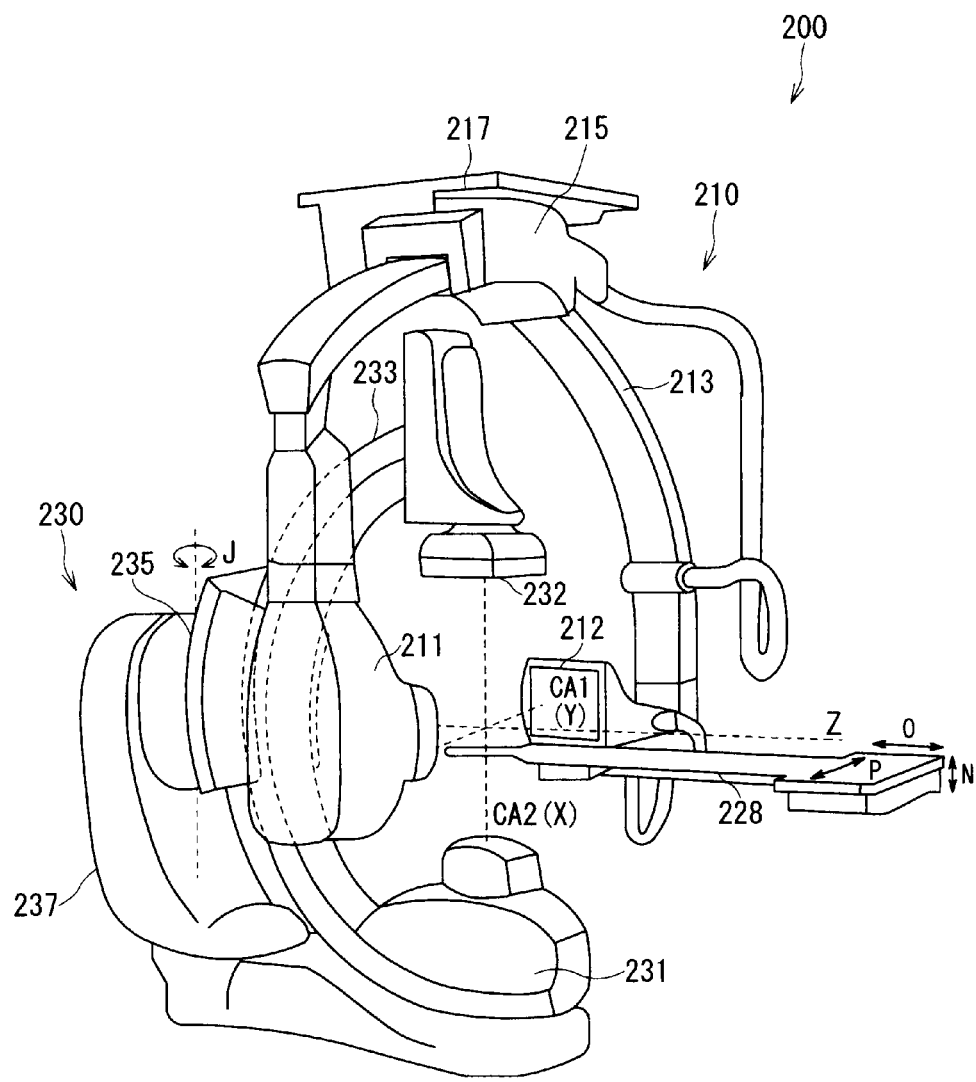
FIG. 3 is a perspective view showing external appearance of an X-ray radiography apparatus according to the embodiment of the present invention.

FIG. 3 shows details of the X-ray radiography apparatus 200. As described above, the X-ray radiography apparatus 200 supports biplane and includes the frontal X-ray radiography system (frontal radiography system 230) and lateral X-ray radiography system (lateral radiography system 210). The X-ray radiography apparatus 200 is designed to be able to radiograph an object placed on a bed 228 simultaneously from two directions: a front direction and lateral direction.

The lateral radiography system 210 includes a first X-ray tube 211 and first X-ray detector 212. The frontal radiography system 230 includes a second X-ray tube 231 and second X-ray detector 232. A combination of an image intensifier and TV camera or a flat panel detector is employed for the X-ray detectors 212 and 232.

The first X-ray tube 211 of the lateral radiography system 210 is mounted at one end of a Ω-arm 213 and the first X-ray detector 212 is mounted at the other end of the Ω-arm 213. Reference character CA1(Y) denotes a first radiographic center axis of the lateral radiography system 210, where the first radiographic center axis CA1(Y) links a focal point of the first X-ray tube 211 with a center of an image-receiving surface of the first X-ray detector 212.

The second X-ray tube 231 of the frontal radiography system 230 is mounted at one end of a C-arm 233 and the second X-ray detector 232 is mounted at the other end of the C-arm 233. Reference character CA2(X) denotes a second radiographic center axis of the frontal radiography system 230, where the second radiographic center axis CA2(X) links a focal point of the second X-ray tube 231 with a center of an image-receiving surface of the second X-ray detector 232.

The first radiographic center axis CA1 of the lateral radiography system 210 and the second radiographic center axis CA2 of the frontal radiography system 230 can be set to intersect each other at a fixed point IC. Position at which the lateral radiography system 210 is located when the first radiographic center axis CA1 passes the fixed point IC is referred to as a shooting position of the lateral radiography system 210 and position at which the frontal radiography system 230 is located when the second radiographic center axis CA2 passes the fixed point IC is referred to as a shooting position of the frontal radiography system 230. A bi-directional shooting position is set up when the lateral radiography system 210 and the frontal radiography system 230 are at their respective shooting positions.

In the lateral radiography system 210, the ceiling-hung, arc-shaped, lateral Ω-arm 213 is suspended from a slider base 217 via a Ω-arm holder 215. The slider base 217 is engaged with a traveling rail installed on a ceiling surface and is supported in such a way as to be able to move lengthwise and crosswise.

In the frontal radiography system 230, the floor-mounted, arc-shaped, C-arm 233 is supported on a stand 237 installed on a floor, via a C-arm holder 235. The stand 237 is structured to be able to swivel along arrow J. By swiveling along arrow J, the frontal radiography system 230 can move between (bi-directional) shooting position located on an inner side of the Ω-arm 213 and waiting position.

A table 228 is supported on a bed in such a way as to be able to move up and down in an up-and-down direction N parallel to an X-axis direction and able to slide in a direction O parallel to a long axis direction Z and direction P parallel to a Y-axis direction. The lateral radiography system 210 and frontal radiography system 230 perform radiographic operations with their movement being controlled by a control apparatus, for example, such that an intersection point between the first radiographic center axis CA1 and second radiographic center axis CA2 will coincide with a region of interest of the object, where the first radiographic center axis CA1 corresponds to the first X-ray tube 211 and first X-ray detector 212 while the second radiographic center axis CA2 corresponds to the second X-ray tube 231 and second X-ray detector 232.

Next, operation of the medical image processing apparatus 100 with the above configuration will be described by citing multiple examples. In all the operation examples, the object's X-ray image data acquired by the X-ray radiography apparatus 200 in advance and transmitted via the network interface unit 10 is being displayed on the display unit 2 as sectional views and a 3D-DSA image in locations shown in FIG. 2.

FIRST EXAMPLE

Figure 4:
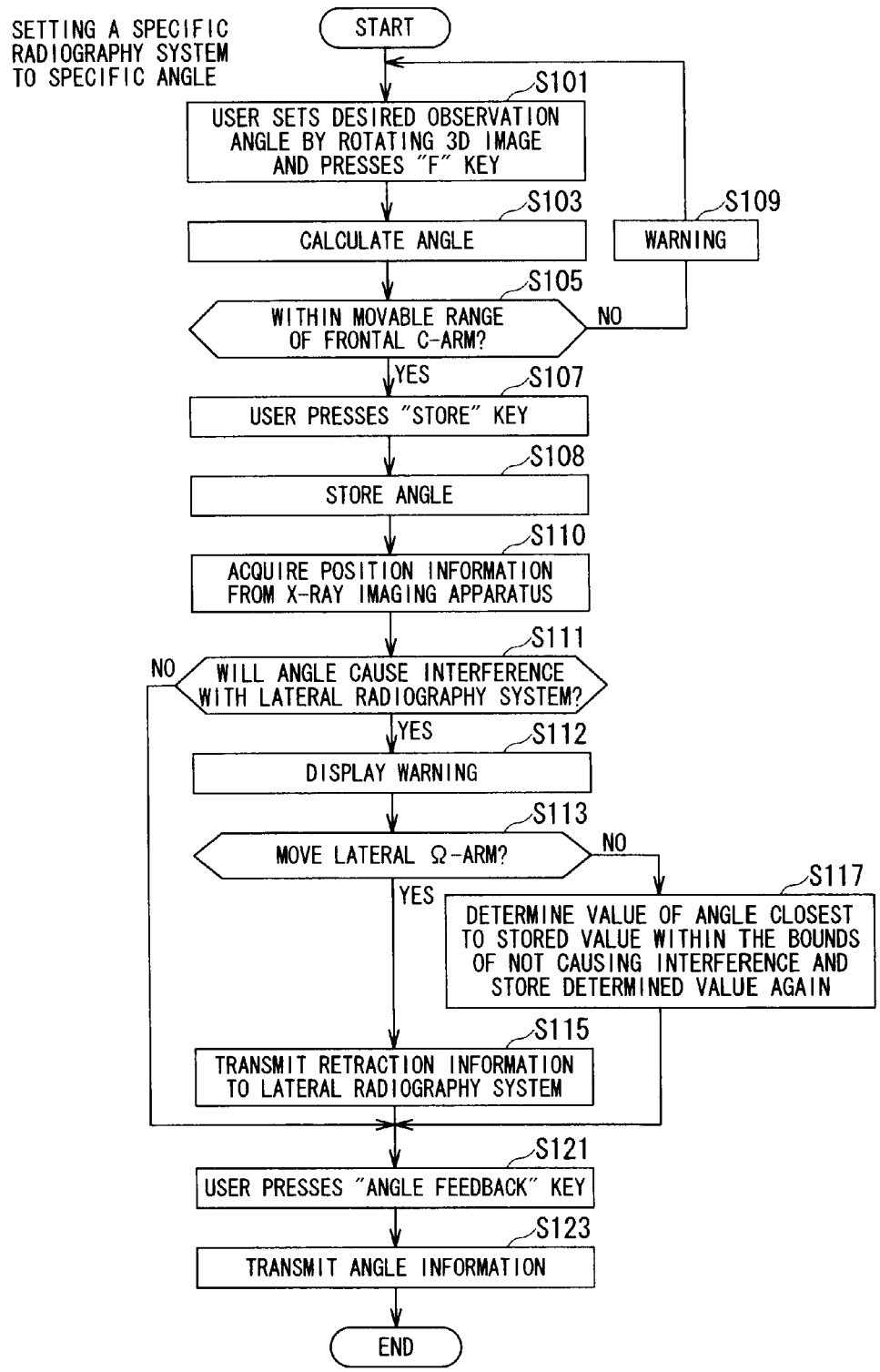
FIG. 4 is a flowchart showing procedures for setting one radiography system (frontal radiography system) to a specific angle, according to a first example of the embodiment of the present invention.

A first example in which specific one of the two radiography systems—frontal and lateral—is set to a specific angle will be described with reference to FIG. 4. It is assumed here that the specific radiography system is the frontal radiography system 230.

Using the mouse of the console unit 5, the user rotates a 3D-DSA image displayed in the "3D" section, thereby setting the F-side (front direction) angle to a desired observation angle of the user, i.e., inputting a projection direction of the F-side, and then presses the "F" key displayed on the display unit 2 (Step S101). By pressing the "F" key, the user specifies the frontal radiography system 230 out of the two radiography systems: frontal and lateral. Incidentally, to select the lateral radiography system 210, the user can press the "L" key. The angle calculation unit 4 calculates the F-side angle from the 3D-DSA image and displays the calculated angle to the right of the "F" key (Step S103). If the F-side angle of the 3D-DSA image is within a movable range of the C-arm 233 of the frontal radiography system 230 (Yes in Step S105), no warning or the like is displayed on the screen. By maintaining the F-side angle, the user presses the "STORE" key of the console unit 5 (Step S107). The storage unit 11 stores the current F-side angle (Step S108). If the F-side angle of the 3D-DSA image is outside the movable range of the C-arm 233 of the frontal radiography system 230 (No in Step S105), the display unit 2 gives an error warning by displaying the angle to the right of the "F" key in red or displaying the icon of the object in the lower part of the "3D" section in red (Step S109) and thereby prompts the user to adjust the angle again.

In Step S110, the medical image processing apparatus 100 acquires current position information about the lateral radiography system 210 and frontal radiography system 230 from the X-ray radiography apparatus 200. The interference checking unit 132 of the interference control unit 13 determines whether the F-side angle stored in Step S108 is likely to cause interference with the lateral radiography system 210 (Step S111). If the F-side angle is likely to cause interference (Yes in Step S111), the warning information output unit 133 of the interference control unit 13 makes the display unit 2 give an error warning by displaying the angle to the right of the "L" key in yellow or displaying the icon of the object in the lower part of the "3D" section in yellow (Step S112). Also, the interference control unit 13 displays a dialog in the display unit 2, asking the user whether to move the Ω-arm 213 of the lateral radiography system 210 (Step S113) to avoid interference. If the user chooses to move the Ω-arm 213 (Yes in Step S113), the retraction information transmission unit 135 of the interference control unit 13 transmits retraction information about the lateral radiography system 210 to the X-ray radiography apparatus 200 via the network interface unit 10 (Step S115). If the user chooses not to move the Ω-arm 213 (No in Step S113), the angle changing unit 134 of the interference control unit 13 determines the value of the F-side angle closest to the value of the F-side angle stored in Step S108 within the bounds of not interfering with the lateral radiography system 210 and stores the determined value again in the storage unit 11 (Step S117).

Once the angle of the frontal radiography system 230 which will not cause interference with the lateral radiography system 210 is determined through the above operations, the user presses the "ANGLE FEEDBACK" key (Step S121). The CPU 1 transmits F-side angle information stored in the storage unit 11 to the X-ray radiography apparatus 200 via the network interface unit 10 (Step S123).

SECOND EXAMPLE

Figure 5:
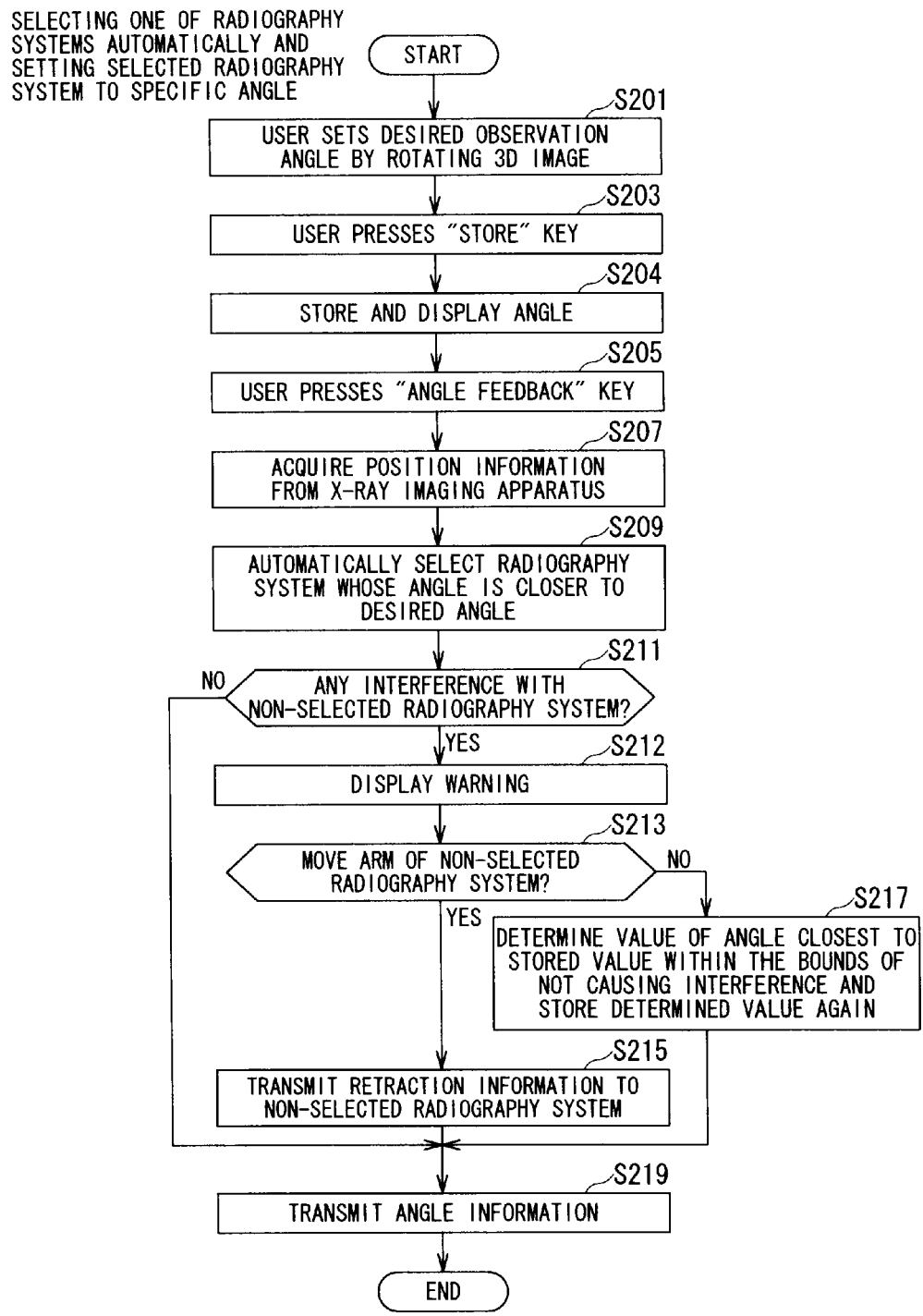
FIG. 5 is a flowchart showing procedures for setting an arbitrary radiography system to a specific angle, according to the embodiment of the present invention.

A second example in which one of the frontal and lateral radiography systems is selected automatically and set to a specific angle to the selected one without making the user specify any of the radiography systems will be described with reference to FIG. 5.

Using the mouse, the user sets the 3D-DSA image displayed in the display unit 2 to the desired observation angle of the user (Step S201), and then presses the "STORE" key (Step S203). The angle calculation unit 4 calculates the angle, stores the angle in the storage unit 11, and displays the angle to the right of the "STORE" key (Step S204). Next, when the user presses the "ANGLE FEEDBACK" key (Step S205), the position information acquisition unit 9 acquires current position information about the frontal radiography system 230 and lateral radiography system 210 (angles and positions of the radiography systems) from the X-ray radiography apparatus 200 via the network interface unit 10 (Step S207).

Next, the CPU 1 determines which of the radiography systems' current angles acquired in Step S207 is closer to the angle stored in Step S204 and selects the radiography system whose angle value is closer. Then, in the display unit 2, the CPU 1 displays the angle stored in Step S204 to the right of the "F" key or "L" key depending on the selected radiography system and erases the display to the right of the "STORE" key (Step S209). For example, if the angle of the lateral radiography system 210 acquired by the position information acquisition unit 9 in Step S207 is closer to the angle stored in Step S204 than the F-side angle, the CPU 1 selects the lateral radiography system 210 and causes the angle displayed to the right of the "STORE" key to be moved to the right of the "L" key in the display unit 2.

Next, the interference checking unit 132 determines whether the selected radiography system is likely to interfere with the other radiography system (the frontal radiography system 230, in this example) (Step S211) when the radiography system selected in Step S209 (the lateral radiography system 210, in this example) is set to the angle stored in Step S204. If interfere is likely to occur (Yes in Step S211), the warning information output unit 133 gives a warning by displaying the icon of the object in yellow in the lower part of the "3D" section in the display unit 2 (Step S212). The interference control unit 13 displays a dialog in the display unit 2, asking the user whether to move the non-selected radiography system (C-arm 233 of the frontal radiography system 230) in order to avoid interference (Step S213). If the user chooses to move the C-arm (Yes in Step S213), the retraction information transmission unit 135 transmits retraction information about the frontal radiography system 230 to the X-ray radiography apparatus 200 via the network interface unit 10 (Step S215). If the user chooses not to move the C-arm 233 (No in Step S213), the angle changing unit 134 determines the value of the angle closest to the value of the angle set first, within the bounds of not causing interference, and stores the determined angle value again in the storage unit 11 (Step S217).

Through the above operations, the radiography system closer to the desired observation angle (frontal radiography system 230) is selected automatically and the selected radiography system is automatically set to the desired observation angle. In so doing, if it is likely that the selected radiography system will interfere with the other radiography system, the angle closest to the desired observation angle within the bounds of not causing interference is determined as a set angle. The CPU 1 transmits the established angle information for the selected radiography system to the X-ray radiography apparatus 200 via the network interface unit 10 (Step S219).

Since it takes time to move the arms of radiography systems, the above operation is useful in minimizing arm travel distance from the current position and setting the radiography system to the desired observation angle of the user in a short time.

THIRD EXAMPLE

Figure 6:
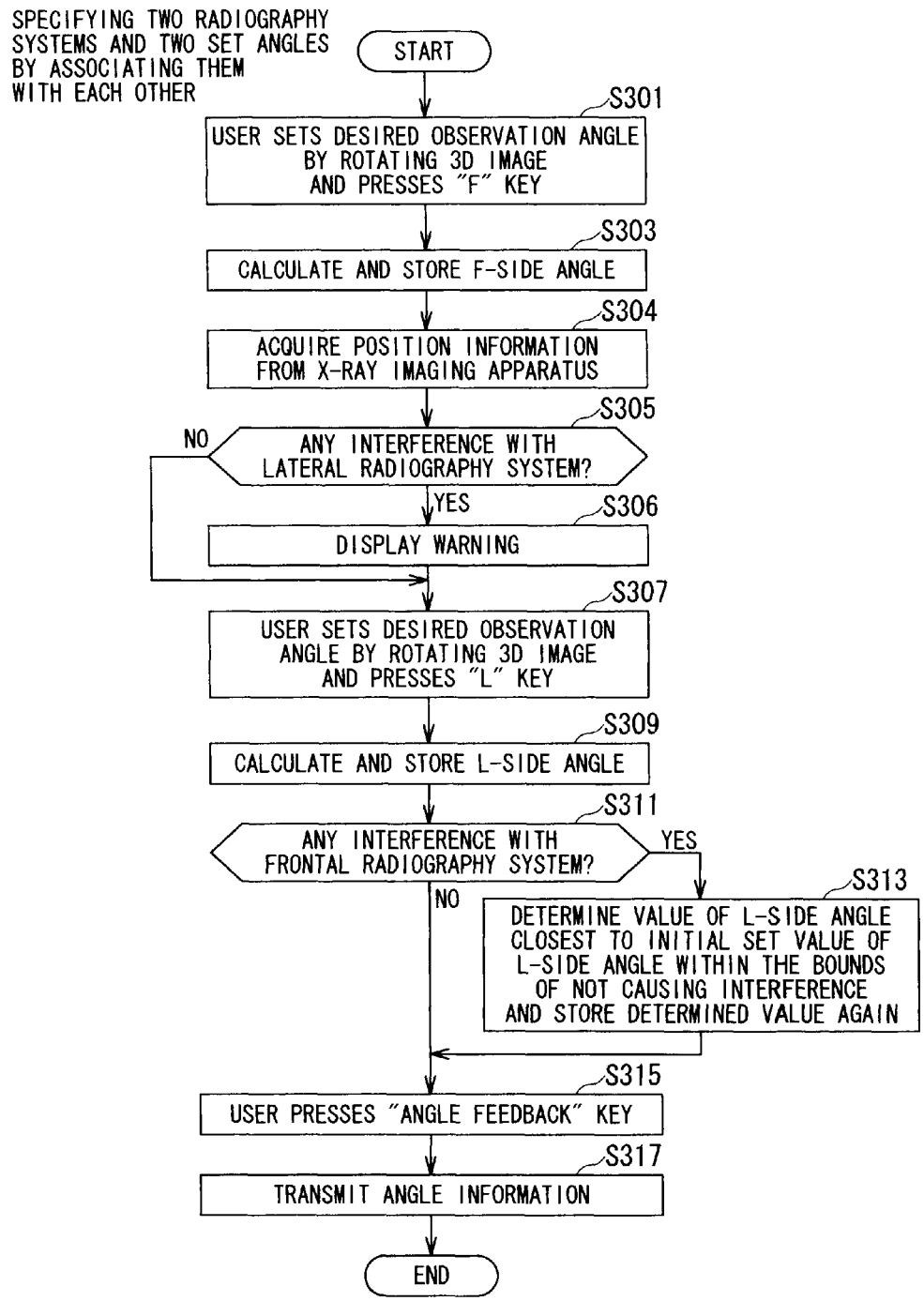
FIG. 6 is a flowchart showing procedures for setting two radiography systems to specific angles in sequence, according to the embodiment of the present invention.

A third example in which two radiography systems and two set angles are specified by being associated with each other will be described with reference to FIG. 6.

First, the F-side angle is set. Using the mouse, the user rotates the 3D-DSA image displayed in the "3D" section of the display unit 2, thereby setting the F-side (front direction) angle to the desired observation angle of the user, i.e., inputting a projection direction of the F-side, and then presses the "F" key (Step S301). The angle calculation unit 4 calculates the F-side angle and displays the angle to the right of the "F" key. The storage unit 11 stores the F-side angle (Step S303).

In Step S304, the medical image processing apparatus 100 acquires current position information about the lateral radiography system 210 and frontal radiography system 230 from the X-ray imaging apparatus 200. Next, the interference checking unit 132 determines whether the F-side angle stored in Step S303 is likely to encounter interference from the lateral radiography system 210 (Step S305). If the F-side angle is likely to encounter interference, the warning information output unit 133 makes the display unit 2 give an warning by displaying the angle to the right of the "L" key in yellow or displaying the icon of the object in the lower part of the "3D" section in yellow (Step S306).

Using the mouse, the user rotates a 3D-DSA image displayed in the display unit 2, thereby setting the L-side (lateral direction) angle to the desired observation angle of the user, i.e., inputting a projection direction of the L-side, and then presses the "L" key (Step S307). The angle calculation unit 4 calculates the L-side angle and displays the calculated angle to the right of the "L" key. The storage unit 11 stores the L-side angle (Step S309). If the L-side angle stored in Step S309 is likely to cause interference with the frontal radiography system 230 (Yes in Step S311), the angle changing unit 134 determines the value of the L-side angle closest to the initially set value of the L-side angle within the bounds of not causing interference and stores the determined value again in the storage unit 11 (Step S313).

Once the angles of the frontal radiography system 230 and the lateral radiography system 210 which will not cause interference with each other are determined through the above operations, the user presses the "ANGLE FEEDBACK" key (Step S315). The CPU 1 transmits F-side and L-side angle information to the X-ray radiography apparatus 200 via the network interface unit 10 (Step S317).

If there is a likelihood of interference between the two radiography systems, priority is given to the radiography system selected first. In the above example, since the user has selected the frontal radiography system by pressing the "F" key in Step S301, the set angle of the lateral radiography system is corrected without any change to the set angle of the frontal radiography system.

FOURTH EXAMPLE

Figure 7:
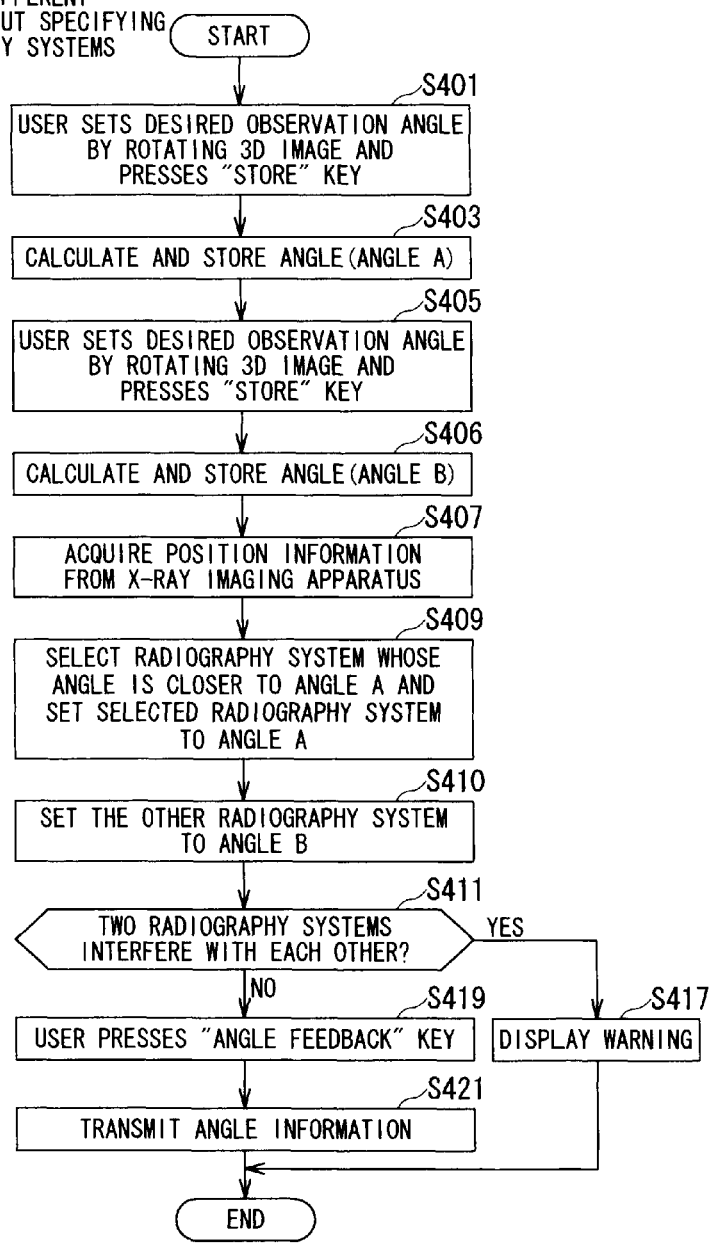
FIG. 7 is a flowchart showing procedures for setting two radiography systems to specific angles in an arbitrary sequence, according to the embodiment of the present invention.

A fourth example in which the two radiography systems are set to specific angles different from each other without making the user specify any of the two radiography systems will be described with reference to FIG. 7.

Using the mouse, the user sets the 3D-DSA image displayed in the display unit 2 to a desired observation angle of the user, and then presses the "STORE" key (Step S401). The angle calculation unit 4 calculates the angle, stores the angle A in the storage unit 11, and displays the angle A to the right of the "STORE" key (Step S403). Next, the user sets the 3D-DSA image to another desired observation angle, and then presses the "STORE" key (Step S405). The angle calculation unit 4 calculates the corresponding angle on the image and stores the angle B in the storage unit 11 as well (Step S406). The position information acquisition unit 9 acquires current position information about the frontal radiography system 230 and lateral radiography system 210 (angles and positions of the radiography systems) from the X-ray radiography apparatus 200 via the network interface unit 10 (Step S407).

Next, the CPU 1 compares the current angles of the radiography systems acquired in Step S407 with the angle A stored in Step S403, automatically selects the radiography system with a closer value, and sets the selected radiography system to the angle A (Step S409). For example, if an angle difference ΔAL between the angle A and the angle of the lateral radiography system 210 is smaller than an angle difference ΔAF between the angle A and the angle of the frontal radiography system 230, the CPU 1 sets the lateral radiography system 210 to the angle A, where the angle A has been stored in the storage unit 11 in Step S403 and the angles of the lateral radiography system 210 and frontal radiography system 230 are contained in the position information acquired by the position information acquisition unit 9 in Step S407. Then, the CPU 1 sets the other radiography system, i.e., the frontal radiography system 230, to the angle B stored in Step S406 (Step S410).

Next, the interference checking unit 132 determines whether the two radiography systems will interfere with each other (Step S411). If the angle of the lateral radiography system 210 or frontal radiography system 230 cannot be set due to interference (No in Step S411), the warning information output unit 133 displays an error warning in the display unit 2 (Step S417).

If both A and B are available to be set for the frontal radiography system 230 and lateral radiography system 210, the angle calculation unit 4 calculates an amount of angle change required when the angle of the lateral radiography system 210 is set to A and the angle of the frontal radiography system 230 is set to B as well as an amount of angle change required when the angle of the lateral radiography system 210 is set to B and the angle of the frontal radiography system 230 is set to A. Then, the angle calculation unit 4 selects the setting which requires a shorter time for angle change.

Once the angles of the frontal radiography system 230 and lateral radiography system 210 which will not cause interference are determined through the above operations, the user presses the "ANGLE FEEDBACK" key (Step S419). The CPU 1 transmits F-side and L-side angle information to the X-ray radiography apparatus 200 via the network interface unit 10 (Step S421).

In this way, since the desired observation angles of the user can be set using a 3D-DSA image and transmitted to the radiography systems, a region desired to be observed can be displayed exactly without interference between the two radiography systems, making it easy to diagnose the subject using images.

Incidentally, the examples described above can work either individually or in combination.

Although in the first and third example, when the user presses the "F" key after rotating the 3D-DSA image by a desired angle, the angle calculation unit 4 performs angle calculations and then the interference checking unit 132 checks for interference with the lateral radiography system, the user may select a radiography system by pressing the appropriate key before rotating the 3D-DSA image. For example, in the first example, the user presses the "F" key first. In this state, the position information acquisition unit 9 acquires information about the current position and angle of the frontal radiography system. Next, when the user rotates the 3D-DSA image, the interference checking unit 132 determines whether the position and angle fall within a movable range of the frontal radiography system and then checks for interference with the lateral radiography system. This makes it possible to determine the angle by referring to interference checking information in real time.

Although in the second and fourth example, the radiography system with a smaller angle difference between a desired angle and an actual angle of the radiography system is selected, alternatively a radiography system may be selected based on the time required to set the radiography system to the desired angle, position of the radiography system, presence or absence of interference, possibility of contact with the patient or surgeon, or the like.

Also, as shown in FIG. 2, a "SIMULTANEOUS" key may be further displayed on the right side of the display unit 2. When the "SIMULTANEOUS" key is pressed, the display unit 2 displays two three-dimensional images, for example, 90 degrees apart from each other in the "3D" section on the right side. When one of the images is rotated using the mouse, the other image rotates together, remaining 90-degrees displaced. Incidentally, the frontal radiography system and lateral radiography system can be operated so as to avoid an angle at which the two systems will interfere with each other.

Further, an "OK" key and a "Retry" key may be additionally displayed on a part of the display unit 2. In the above description, when the "ANGLE FEEDBACK" key is pressed, F-side and/or L-side angle information is immediately transmitted to the X-ray radiography apparatus 200. Alternatively, before transmitting the angle information, a blood vessel image which is to be observed from a inputted projection direction of F-side and/or L-side may be displayed on the display unit 2 for the purpose of confirmation. Then, when the "OK" key is pressed, angle information corresponding to the projection direction may be transmitted to the X-ray radiography apparatus 200. On the other hand, when the "Retry" key is pressed, the display unit 2 may display again the window for inputting the projection direction without transmitting the current angle information.

Also, the medical image processing apparatus 100 may be connected with an X-ray radiography apparatus 200 equipped with a single radiography system. In that case, the angle calculation unit 4 can be switched to a mode only for setting an angle in a single direction.

Thus far, the medical image processing apparatus 100 and the X-ray radiography apparatus 200 are explained as independent apparatuses from each other. Instead, the X-ray radiography apparatus 200 may be configured so as to include the medical image processing apparatus 100 (This configuration may be referred to as a medical apparatus). By contrast, the medical image processing apparatus 100 may be configured so as to include the X-ray radiography apparatus 200 (This configuration also may be referred to as a medical apparatus).

Further thus far, examples are described where a 3D image acquired by the X-ray radiography apparatus 200 is displayed on the display unit 2 of the medical image processing apparatus 100, and the inputted projection direction using the 3D image is transmitted to the same X-ray radiography apparatus 200 as "angle feedback" information. However, the 3D image for inputting the projection direction is not necessarily acquired from the same X-ray radiography apparatus 200. Instead, for example, the 3D image may be acquired from another X-ray radiography apparatus, an X-ray CT apparatus, or an MRI apparatus other than the X-ray radiography apparatus 200.

While certain embodiments have been described, these embodiments have been presented by way of example only, and are not intended to limit the scope of the invention. Indeed, the novel apparatuses and units described herein may be embodied in a variety of other forms; furthermore, various omissions, substitutions and changes in the form of the apparatuses and units described herein may be made without departing from the spirit of the invention. The accompanying claims and their equivalents are intended to cover such forms or modifications as would fall within the scope and spirit of the invention.

What is claimed is:

1. A medical apparatus which is connected to an X-ray radiography apparatus and displays an image of an object collected by using a first radiography system and a second radiography system of the X-ray radiography apparatus, the medical apparatus comprising:
   an image processing unit configured to acquire a three-dimensional image;
   a projection direction input unit configured to input a projection direction for at least one of the first radiography system and the second radiography system using the three-dimensional image;
   an imaging direction setting unit configured to set an imaging direction for at least one of the first radiography system and the second radiography system based on the projection direction; and
   a mechanical interference checking unit configured to determine whether mechanical interference between the first radiography system and the second radiography system will occur if one of the first radiography system and the second radiography system is moved in accordance with the set imaging direction, before transmitting the imaging direction to the X-ray radiography apparatus to move the one of the first radiography system and the second radiography system.

2. The medical image processing apparatus according to claim 1, further comprising a display, wherein
   if it is determined that the mechanical interference will occur, the mechanical interference checking unit outputs warning information to that effect to the display.

3. The medical image processing apparatus according to claim 1, wherein:
   the projection direction input unit is configured to select one of the first radiography system and the second radiography system and then input the projection direction for the selected radiography system by rotating the three-dimensional image in a desired direction; and
   the mechanical interference checking unit is configured to determine, during the rotation of the three-dimensional image, whether the selected radiography system will mechanically interfere with the non-selected radiography system.

4. The medical image processing apparatus according to claim 3, further comprising a display, wherein
   if it is determined that the mechanical interference will occur, the mechanical interference checking unit outputs warning information to that effect to the display.

5. The medical image processing apparatus according to claim 1, further comprising a projection processing unit configured to generate a projected image from the projection direction using at least one of the first radiography system and the second radiography system.

6. The medical image processing apparatus according to claim 1, wherein the image processing unit is configured to acquire the three-dimensional image based on the X-ray image data collected by at least one of the first radiography system and the second radiography system.

7. A medical apparatus which is connected to an X-ray radiography apparatus and displays an image of an object collected by using a first radiography system and a second radiography system of the X-ray radiography apparatus, the medical apparatus comprising:
   an image processing unit configured to acquire a three-dimensional image;
   a projection direction input unit configured to input a projection direction for at least one of the first radiography system and the second radiography system using the three-dimensional image;
   a position information input unit configured to input current position information about the first radiography system and the second radiography system;
   an imaging direction setting unit configured to set an imaging direction for at least one of the first radiography system and the second radiography system based on the projection direction and the current position information such that the first radiography system and the second radiography system do not mechanically interfere with each other; and
   a mechanical interference checking unit configured to determine whether mechanical interference between the first radiography system and the second radiography system will occur if one of the first radiography system and the second radiography system is moved in accordance with the set imaging direction, before transmitting the imaging direction to the X-ray radiography apparatus to move the one of the first radiography system and the second radiography system.

8. The medical image processing apparatus according to claim 7, wherein the image direction setting unit is configured to set the imaging direction by selecting one of the first radiography system and the second radiography system;
   a single projection direction is inputted via the projection direction input unit; and
   the imaging direction setting unit is configured to compare the current position information of the first radiography system and the second radiography system with the single projection direction, select the radiography system with a smaller difference from the projection direction, and set the selected radiography system to the imaging direction corresponding to the single projection direction.

9. The medical image processing apparatus according to claim 7, wherein the image direction setting unit is configured to set the imaging direction for both the first radiography system and the second radiography system;
   a first projection direction and a second projection direction are inputted via the projection direction input unit; and
   the imaging direction setting unit is configured to compare the current position information of the first radiography system and the second radiography system with the first projection direction, select the radiography system with a smaller difference from the first projection direction as an radiography system corresponding to the first projection direction, and set the selected radiography system to the imaging direction corresponding to the first projection direction while setting the other radiography system to the imaging direction corresponding to the second projection direction.

10. The medical image processing apparatus according to claim 9, wherein in the projection direction input unit, a projection direction inputted first is designated as the first projection direction and a projection direction inputted next is designated as the second projection direction.

11. The medical image processing apparatus according to claim 7, further comprising a projection processing unit configured to generate a projected image from the projection direction using at least one of the first radiography system and the second radiography system.

12. The medical image processing apparatus according to claim 7, wherein the image processing unit is configured to acquire the three-dimensional image based on the X-ray image data collected by at least one of the first radiography system and the second radiography system.

13. A medical apparatus which is connected to an X-ray radiography apparatus and displays an image of an object collected by using a first radiography system and a second radiography system of the X-ray radiography apparatus, the medical apparatus comprising:
 an image processing unit configured to acquire a three-dimensional image;
 a projection direction input unit configured to input a projection direction for at least one of the first radiography system and the second radiography system using the three-dimensional image;
 an imaging direction setting unit configured to set an imaging direction for at least one of the first radiography system and the second radiography system based on the projection direction; and
 a mechanical interference checking unit configured to determine whether mechanical interference between the first radiography system and the second radiography system will occur if one of the first radiography system and the second radiography system is moved in accordance with the set imaging direction, before transmitting the imaging direction to the X-ray radiography apparatus to move the one of the first radiography system and the second radiography system,
 wherein the imaging direction setting unit is configured to set the imaging direction so as to avoid mechanical interference between the first radiography system and the second radiography system.

14. The medical image processing apparatus according to claim 13, wherein the image direction setting unit is configured to set the imaging direction by selecting one of the first radiography system and the second radiography system;
 a single projection direction is inputted via the projection direction input unit; and
 if it is determined that the first radiography system and the second radiography system will mechanically interfere with each other, the imaging direction setting unit sets the selected radiography system to the imaging direction corresponding to the projection direction and retracts the non-selected radiography system to a location where no mechanical interference will occur.

15. The medical image processing apparatus according to claim 13, wherein the image direction setting unit is configured to set the imaging direction for both the first radiography system and the second radiography system;
 a first projection direction and a second projection direction are inputted via the projection direction input unit by being associated with the first radiography system and the second radiography system, respectively; and
 if it is determined that the first radiography system and the second radiography system will mechanically interfere with each other, the imaging direction setting unit sets the first radiography system to the imaging direction corresponding to the first projection direction while setting the second radiography system to the imaging direction corresponding to the direction closest to the second projection direction within the bounds of not causing mechanical interference.

16. The medical image processing apparatus according to claim 15, wherein in the projection direction input unit, a projection direction inputted first is designated as the first projection direction and a projection direction inputted next is designated as the second projection direction.

17. The medical image processing apparatus according to claim 13, further comprising a projection processing unit configured to generate a projected image using at least one of the first radiography system and the second radiography system after moving at least one of the first radiography system and the second radiography system in the imaging direction.

18. A control method of a medical apparatus which is connected to an X-ray radiography apparatus and displays an image of an object collected by using a first radiography system and a second radiography system of the X-ray radiography apparatus, the method comprising:
 acquiring a three-dimensional image;
 inputting a projection direction for at least one of the first radiography system and the second radiography system using the three-dimensional image;
 setting an imaging direction for at least one of the first radiography system and the second radiography system based on the projection direction; and
 determining whether mechanical interference between the first radiography system and the second radiography system will occur if one of the first radiography system and the second radiography system is moved in accordance with the set imaging direction, before transmitting the imaging direction to the X-ray radiography apparatus to move the one of the first radiography system and the second radiography system.

19. A control method of a medical apparatus which is connected to an X-ray radiography apparatus and displays an image of an object collected by using a first radiography system and a second radiography system of the X-ray radiography apparatus, the method comprising:
 acquiring a three-dimensional image;
 inputting a projection direction for at least one of the first radiography system and the second radiography system using the three-dimensional image;
 inputting current position information about the first radiography system and the second radiography system;
 setting an imaging direction for at least one of the first radiography system and the second radiography system based on the projection direction and the current position information such that the first radiography system and the second radiography system do not mechanically interfere with each other; and
 determining whether mechanical interference between the first radiography system and the second radiography system will occur if one of the first radiography system and the second radiography system is moved in accordance with the set imaging direction, before transmitting the imaging direction to the X-ray radiography apparatus to move the one of the first radiography system and the second radiography system.

20. A control method of a medical apparatus which is connected to an X-ray radiography apparatus and displays an image of an object collected by using a first radiography system and a second radiography system of the X-ray radiography apparatus, the method comprising:

acquiring a three-dimensional image;

inputting a projection direction for at least one of the first radiography system and the second radiography system using the three-dimensional image;

setting an imaging direction for at least one of the first radiography system and the second radiography system based on the projection direction; and determining whether mechanical interference between the first radiography system and the second radiography system will occur if one of the first radiography system and the second radiography system is moved in accordance with the set imaging direction, before transmitting the imaging direction to the X-ray radiography apparatus to move the one of the first radiography system and the second radiography system, wherein in the step of setting the imaging direction, the imaging direction is set so as to avoid mechanical interference between the first radiography system and the second radiography system.

* * * * *